(12) United States Patent
Billington et al.

(10) Patent No.: US 7,887,893 B2
(45) Date of Patent: Feb. 15, 2011

(54) BACTERIAL POLY(HYDROXY ALKANOATE) POLYMER AND NATURAL FIBER COMPOSITES

(75) Inventors: Sarah L. Billington, Palo Alto, CA (US); Craig S. Criddle, Cupertino, CA (US); Curtis W. Frank, Cupertino, CA (US); Margaret C. Morse, Stanford, CA (US); Sarah J. Christian, Stanford, CA (US); Allison J. Pieja, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 575 days.

(21) Appl. No.: 12/002,001

(22) Filed: Dec. 12, 2007

(65) Prior Publication Data

US 2008/0160567 A1   Jul. 3, 2008

Related U.S. Application Data

(60) Provisional application No. 60/874,559, filed on Dec. 12, 2006.

(51) Int. Cl.
*C12P 7/62* (2006.01)
*B27N 3/02* (2006.01)
*B27N 3/04* (2006.01)
*B27N 3/12* (2006.01)

(52) U.S. Cl. .................. 428/36.2; 428/36.1; 435/135
(58) Field of Classification Search .............. None
See application file for complete search history.

(56) References Cited

U.S. PATENT DOCUMENTS

| 7,141,400 B2 * | 11/2006 | Yu .......................... 435/135 |
| 7,288,618 B2 * | 10/2007 | Bastioli et al. ............ 528/275 |
| 2005/0215672 A1 * | 9/2005 | Mohanty et al. ........... 524/9 |

* cited by examiner

*Primary Examiner*—Herbert J. Lilling
(74) *Attorney, Agent, or Firm*—Lumen Patent Firm

(57) ABSTRACT

A biocomposite is produced from natural fiber fabrics embedded in a matrix of biosynthetic polyhydroxy-alkanoate (PHA) polymers. The PHA is synthesized using aerobic microbial biosynthesis using mixed bacterial cultures and a feedstock containing anaerobic degradation products such as methane and volatile fatty acids derived from microbial biodegradation of organic waste materials, which may include waste biocomposites. Monomers may be added to the synthesized PHA polymer to control mechanical properties of the resulting biocomposite. The natural fibers and/or PHA may be pretreated using various techniques to improve the bond between the fibers and the PHA resin matrix and water absorption resistance of the fibers. The composite may be a laminate of treated and untreated fabric layers, or differently treated layers, to achieve good in-service performance as well as rapid and/or optimal biogas production when taken out of service and put in an anaerobic environment to degrade.

9 Claims, 3 Drawing Sheets

BACTERIAL POLY(HYDROXY ALKANOATE) POLYMER AND NATURAL FIBER COMPOSITES

CROSS-REFERENCE TO RELATED APPLICATIONS

This application claims priority from U.S. Provisional Patent Application 60/874,559 filed Dec. 12, 2006, which is incorporated herein by reference.

FIELD OF THE INVENTION

The present invention relates generally to biocomposite materials and methods for making them. More specifically, it relates to methods for producing biocomposites of natural fibers and poly(hydroxy alkanoate) (PHA) polymers.

BACKGROUND OF THE INVENTION

The use of wood, concrete, steel, and other conventional materials in manufacturing and construction has an adverse impact on the natural environment, both through natural resource depletion, recalcitrance in landfills, and greenhouse gas emissions. Consequently, researchers have been motivated to seek and develop more environmentally benign and preferably biodegradable alternatives. One avenue of research is to develop renewable biocomposite materials that can be biodegraded after taken out of service and used as feedstock to grow material components for new construction, completing the biotransformation cycle. There are, however, several challenges of this approach. First, it is desirable that the renewable materials have structural-grade properties, and that these properties do not degrade after each cycle. Second, it is important that the biotransformation cycle is fast and energy efficient. Third, the various stages of the biotransformation cycle should be inexpensive and easy to implement. Unfortunately, existing biocomposites and their associated biotransformation cycles do not satisfy these criteria as well as desired.

SUMMARY OF THE INVENTION

In one aspect, a method is provided for producing a biocomposite material comprising natural fibers and resins derived from biosynthetic poly(hydroxy alkanoate) (PHA) polymers. Anaerobic microbial biodegradation of waste materials, which may include waste biocomposites, is performed to obtain anaerobic degradation products such as methane and volatile fatty acids (e.g., acetic and propionic acids). These degradation products are collected and used to form a feedstock, which is used in turn for aerobic microbial biosynthesis of PHA polymers using mixed bacterial cultures. PHA granules are extracted from the biosynthesized PHA polymers and the biocomposite material is fabricated from the PHA granules and natural fibers, such as a woven hemp fabric, jute or flax. The fabrication may include various processes including, for example, a hand/wet lay-up process. In one embodiment, multiple layers of a woven natural fiber fabric are embedded in a resin matrix produced from the PHA granules to form a laminate. In one embodiment, the PHA polymers are poly(hydroxy butyrate) (PHB) polymers. The biocomposite matrix material is preferably formed from the PHA and monomer additives such as hydroxyhexanoate (HH), hydroxybutyrate (HB), and hydroxyvalerate (HV). An example is poly-(hydroxybutyrate-covalerate) (PHBV).

The method may include pretreating the natural fibers and/or PHA prior to embedding the fibers in the matrix. The pretreatment may include, for example, treatments with modified PHA, succinic anhydride, and/or maleic anhydride to improve the bond between the fibers and the PHA resin matrix. The method may also include building up of treated and untreated layers, or differently treated layers, to achieve good in-service performance as well as rapid and/or optimal biogas production when taken out of service and put in an anaerobic environment to degrade. Embodiments may also include amending the feedstock with volatile fatty acids derived from biodegradation of organic wastes.

DETAILED DESCRIPTION

In the present description, the term "biocomposite" is defined as a material composed of plant fibers embedded in a resin matrix, where the resin matrix is derived from plants, agricultural waste, municipal waste, anaerobic fermentation products, and/or biocomposites. The term "biodegradation" is defined as a breaking down of organic substances by living organisms, e.g., bacteria. In the present context, biodegradation is intended to include anaerobic fermentation. Similarly, "biosynthesis" is defined as a production of chemical compounds from simpler reagents by living organisms, e.g., bacteria.

Figure 1:
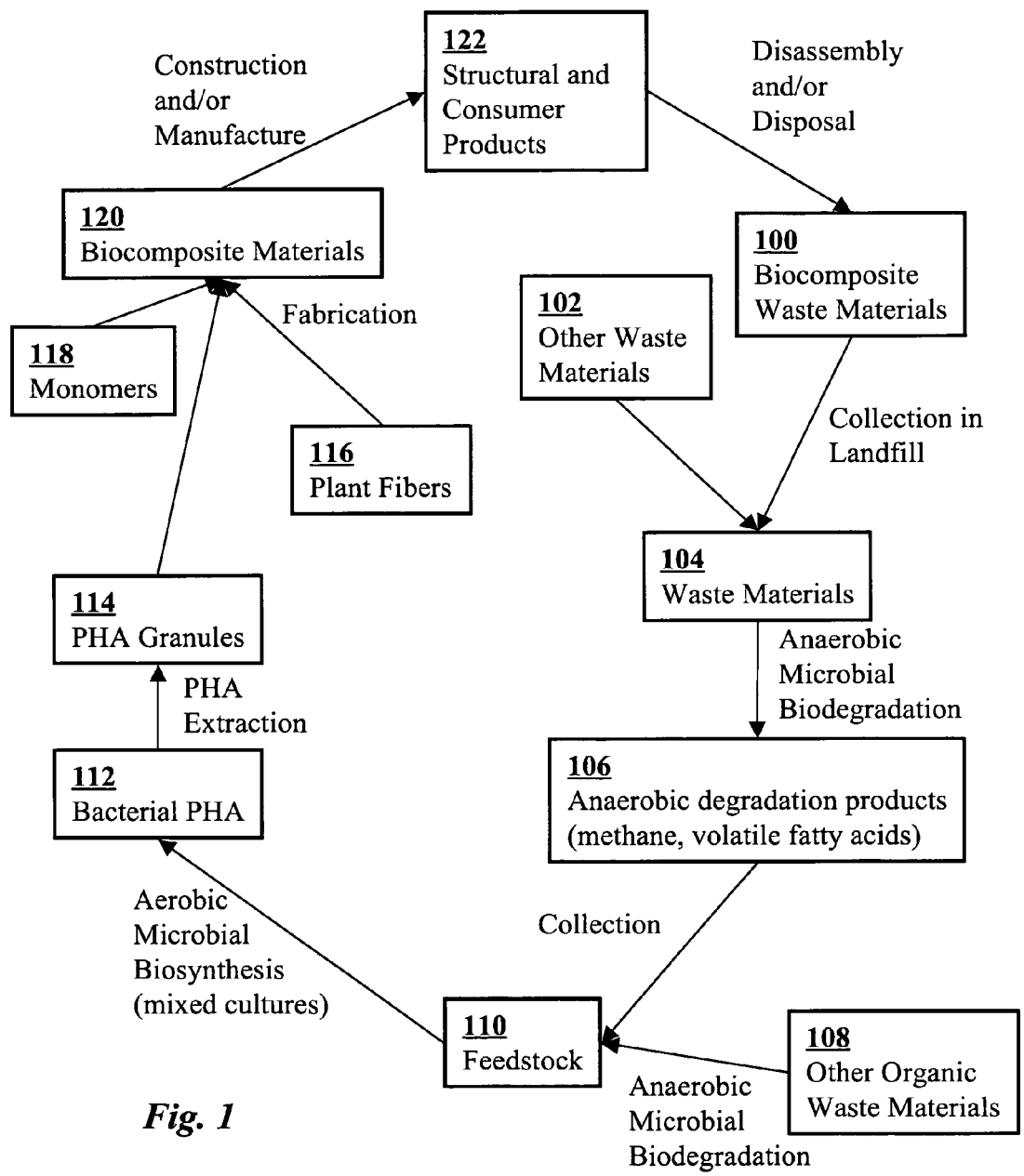
FIG. 1 is a schematic diagram of a biotransformation cycle including steps for producing a biocomposite according to one embodiment of the invention.

FIG. 1 is a schematic diagram of a biotransformation cycle into which the methods of the present invention are intended to fit. Waste materials 104, which may include both biocomposite waste materials 100 as well as other organic solid waste materials 102 are collected in a modern landfill (e.g., anaerobic digester) where they undergo anaerobic microbial biodegradation.

Figure 2:
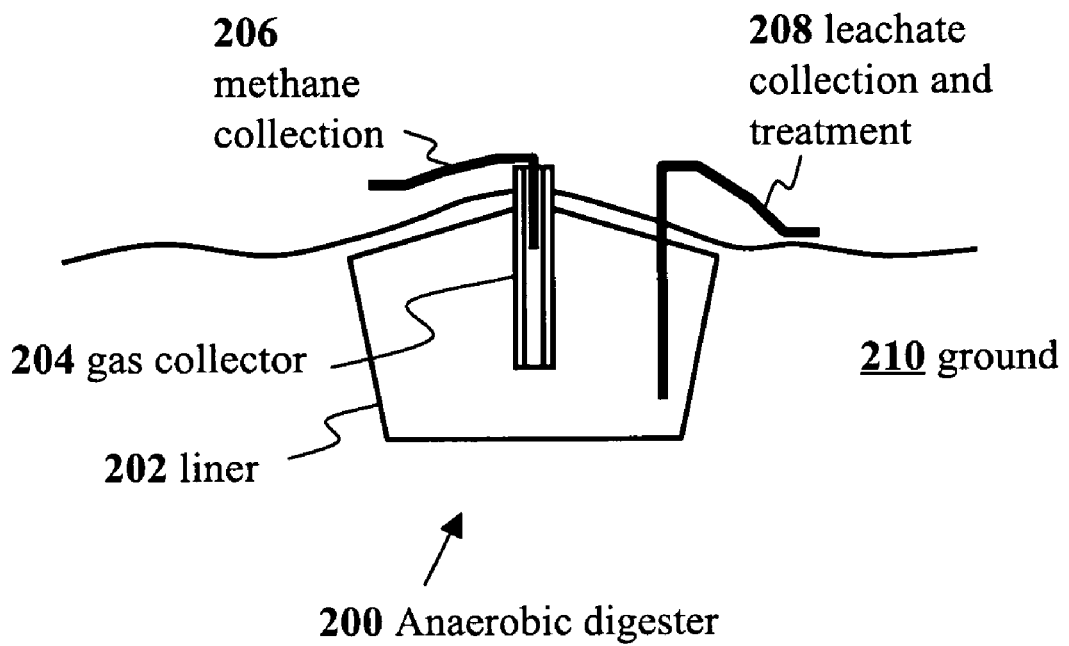
FIG. 2 illustrates an anaerobic digester which may be used to biodegrade waste materials according to one embodiment of the invention.

FIG. 2 illustrates an anaerobic digester 200 which may be used to biodegrade the waste materials. The digester 200 is positioned in the ground 210 just below the surface. A liner 202 forms the walls of the digester into which the organic waste such as biocomposite is placed. A methane gas collector 204 is used to collect methane degradation product of the biodegradation. The methane is then fed from the digester using a methane collection tube 206. A tube 208 is used for leachate collection.

Returning to FIG. 1, anaerobic degradation products 106 of this biodegradation include methane, carbon dioxide, and volatile fatty acids, e.g., acetic and propionic acids. Preferably, the biocomposite materials biodegrade under anaerobic conditions with at least 80% biodegradation within 60 days and with methane production of at least 90% of the theoretical maximum, or with production of equivalent concentrations of acetic and propionic acid. Biodegradation rates may be promoted by creating conditions that enhance microbial colonization and growth, increase hydrolase enzyme concentrations and increase the rates of diffusion of hydrolase enzymes into the materials, by changes in mixing and shear, particle size, PHB/PHV ratios, temperature, pH, buffer, or nutrients. Rates may also be enhanced by the structure and composition of the biocomposite material, e.g., volume fraction of fibers, pre-treatment of fibers, number of layers. Chopping or grinding waste biocomposites may also be used to promote biodegradation. Organisms capable of degrading PHAs are widespread. The initial step in the process is hydrolysis of the polymer to the constituent monomers mediated by a PHA depolymerase, which may be added or produced and secreted by microorganisms that colonize the biocomposite, or it may be accomplished chemically by treatment at low pH. Anaerobically, breakdown of the polymer proceeds to volatile fatty acids, such as acetic acid and propionate, under pH conditions less than 6.2, or to methane, at higher pH.

The degradation products 106 are collected and may be stored temporarily and/or transported. In some cases the degradation products 106 may be combined with anaerobic fermentation products derived from other organic waste products 108, such as agricultural waste streams or treated wastewater, to form a feedstock 110 for subsequent biosynthesis of PHA. The feedstock may be used immediately, stored, or transported. The use of methane and/or volatile fatty acids as a carbon source in the feedstock makes the biosynthesis process less expensive as compared with other microbial processes that use more expensive carbon sources. Methane also can be continuously generated and delivered to a batch culture as a uniform feedstock for growth of methanotrophs and PHA production. The feedstock 110 is used in aerobic microbial biosynthesis of PHA polymers 112 using mixed bacterial cultures, preferably including methanotrophs. The PHA is grown under unbalanced growth conditions, i.e., when an essential nutrient is deficient or when toxic stressors are present. The biosynthesis may be performed using a small-scale fermentation facility.

The mixed cultures used in the biosynthesis of PHA are selected to use the specific biodegradation products 106 of the biodegradation process. The use of mixed bacterial cultures makes the process less expensive as compared with processes that use pure cultures by eliminating the need for maintenance of special cultures. Common aerobic bacteria can be induced to produce PHAs as intracellular granules when the carbon supply exceeds growth requirements. Growth substrates for these organisms include waste organic matter, sugars, volatile fatty acids, and methane. The responsible enzymes are 3-keto thiolase, aceto-acetyl-COA reductase, and PHP synthase. The genes encoding these enzymes are widespread in nature and are induced under unbalanced growth conditions. The mixed cultures may be derived from biomass from a local wastewater treatment plant. Cultures may be grown to high density, subjected to nutrient limitation (e.g., nitrogen (N) and phosphorus (P)), and screened for PHA production in aerobic shake flask cultures. Preferably, a methane-fed culture grown to high cell density is used to produce high percentages of PHA when supplemented with acetate and/or propionate, and limited for N or P. The most effective culture is one with high PHA yield, high rate of PHA production, high growth rate, and high fitness, allowing robust non-sterile operation. This may be achieved by allowing communities to adapt to an environment that provides a selective advantage for PHA production. The biosynthesis may be performed in a bioreactor with conditions maintained to favor high levels of PHA production under non-sterile growth conditions in rapid, high cell density fermentations. A range of bioreactor configurations may be used, including sequencing membrane bioreactors and a continuous multi-stage dispersed growth configuration. Preferably, the bioreactor maintains conditions that select against methanotrophs that either do not produce PHBs or produce them inefficiently. For example, sequencing batch reactors can be operated by cycling through two periods. In the first period there is excess methane but no nutrients, while in the second period there are nutrients but no methane. Repeated cycling through these periods will select for bacteria that produce enough PHB to replicate during the period of carbon starvation. Additional species may be periodically introduced. Organisms able to produce more PHBs more quickly should become dominant. Operating the system in a non-sterile manner ensures that the dominant species has a high relative fitness. However, different methanotrophs will likely produce PHB with differing molecular weight distributions or potentially other PHA polymers. Consequently, the suitability of the PHA polymers for particular target applications serves as an additional criterion for subsequent selection of cultures.

PHAs are polyesters with repeating subunits (100-30,000) that have the formula

—[O—CH(R)(CH$_2$)$_x$CO]—.

The most common type of PHA is poly(hydroxy butyrate) (PHB), where R=CH$_3$ and x=1. Another is poly(hydroxy valerate) (PHV), where R=CH$_2$CH$_3$ and x=1. In a preferred embodiment, the PHA polymers are poly(hydroxy butyrate) (PHB) polymers.

PHA granules 114 are extracted from the biosynthesized bacterial PHA, e.g., using surfactant treatment to remove much of the protein followed by sodium hypochlorite digestion to remove most of the remaining protein, which leaves PHA granules intact. The alkaline waste stream that results from this process would likely be amenable to anaerobic digestion to methane, which could be collected and recycled as part of feedstock 110. Alternatively, other PHA granule extraction methods based on acid-base extraction and sonication may be used.

A biocomposite material 120 is fabricated from the PHA granules 114 and woven natural fibers 116 such as fabrics of hemp, cotton, flax, jute, sisal, coconut, or sugarcane fibers by embedding the natural fiber fabrics in a resin matrix formed by melting the PHA formed in the bacterial granules. As an alternative approach, the PHA granules may treated to remove cellular debris and then processed separately by melt extrusion to form a PHA of desired thickness and width. PHA sheets may then be alternated with natural fiber fabrics in a laminated structure. Fibers are preferably selected to maximize CO$_2$ sequestration and minimize cultivation impacts while still meeting performance criteria.

Mechanical properties of the PHA resin matrix can be altered through copolymerization with other hydroxylalkanoate monomers or with reactive polymer blending. For example, when PHB is copolymerized with hydroxylvalerate (HV) or hydroxyhexanoate (HH), the ductility, toughness, and ease of molding increase while the crystallinity and melting point decrease. Preferably, the resin matrix material is formed from the PHA and monomer additives 118 such as hydroxhexanoate (HH). The monomer units may be introduced into the PHA polymer chain in various volume fractions, e.g., 3.8 mol % to 10 mol %, thereby controlling mechanical properties of the resulting biocomposite, including stress-strain response, ductility, and tensile strength. For example, ductility can be increased and tensile strength decreased by substituting alternative monomers, such as 3-hydroxyvalerate (3HV) for some of the 3-hydroxybutyrate (3HB) units in PHB. Note that reduced matrix tensile strength could be desirable for engineering biocomposites for ductile, multiple-cracking behavior.

The composite fabrication may use a simple hand/wet lay-up process. According to one technique, the melted resin matrix (preferably heated to 175-180 C) may be poured over the natural fiber fabric. The impregnation of the resin into the fibers preferably is then facilitated by applying pressure, e.g., 7-32 psi, with a roller, press, or other method. As an alternative to pouring the resin over the fabric, the fabrics may be submerged in a bath of melted resin, or the fabric may be combined with polymer powder and heated. As yet another alternative, the PHA resin may be separately fabricated into sheets that are then alternated with fabric and the entire assembly heated under pressure to form the biocomposite. Other fabrication processes include hot press, compression molding, and vacuum bagging with or without an oven. Higher pressures used in these processes may provide biocomposites with improved material properties. Another method includes fabricating thin layers of resin in a hot press or vacuum bag in an oven and making resin sheets, allowing the sheets to cool and then building up laminates using layers of fabric with resin sheets in between. These laminate fabrication processes include hot press, compression molding and vacuum bagging with or without an oven.

The biocomposite may be a laminate including multiple layers of a woven natural fiber fabric embedded in a resin matrix. The fabric layers can be arranged with different orientations to provide a biocomposite with desired structural properties. Varying the orientation of laminate may be particularly useful if locally available natural fiber textiles are anisotropic. The use of different volume fractions of fiber vs. matrix material can also be used to control the strength and stiffness of the biocomposite. The combination of the PHA polymer and fabric provides improved stiffness and strength compared with composites made with short individual fibers using, for example, an injection molding process. Depending on the intended use of the biocomposite material being produced, it may be desirable to postprocess or treat the biocomposite in order to reduce its absorption of moisture from the environment during use. This might be done by coating the surface with mineral or organic films that dissolve or degrade under anaerobic conditions. In addition, the natural fiber could be surface modified with hydrophobic silane coupling agents to block any residual hydroxdyl groups that remain after any surface modification to enhance the bonding.

The biocomposites 120 may be used as raw materials for the construction and/or manufacture of structural and consumer products 122. For example, biocomposite structural and non-structural building components may include beams, panels, walls, scaffolding, pipes, roofing, insulated panels, partition walls, wallboard panels, and architectural pre-cast elements. These may be used in a variety of civil structures including bridges and buildings such as for temporary shelter, long-term housing, commercial offices and manufacturing facilities, and storage. Biocomposite components may also be used in the manufacture of consumer products such as furniture, vehicles, storage containers, and packaging. A biocomposite shelter, for example, may be constructed from biocomposite components such as a frame with biocomposite roof panels and non-structural infill walls. Alternatively, a shelter may be constructed from structural biocomposite insulated wall panels with similar roof panels. Given the relatively low stiffness of biocomposites, in civil structures it is preferable to use biocomposite components that maximize geometric stiffness, such as box sections. Depending on the matrix material used, such sections can be built up from compression molded plates, angles or U-shapes or molded around a form using a vacuum-bag. Another example of a biocomposite component is a structural insulated panel with a foam core sandwiched between composite skins. Preferably, during construction, the biocomposite components are connected using methods that facilitate disassembly. Possible connection methods include mechanical joints, universal connectors, bolted connections and embedded elements to facilitate fastening.

When these biocomposite-based products are taken out of service, they may be disassembled and disposed to provide biocomposite waste materials 100, completing the biotransformation cycle. The cycle for these biocomposites is much faster than that of natural wood and allows for a greater diversity and control of structural properties. The efficiency of the cycle and the ease of production make these biocomposites especially useful in the developing world.

Figure 3:
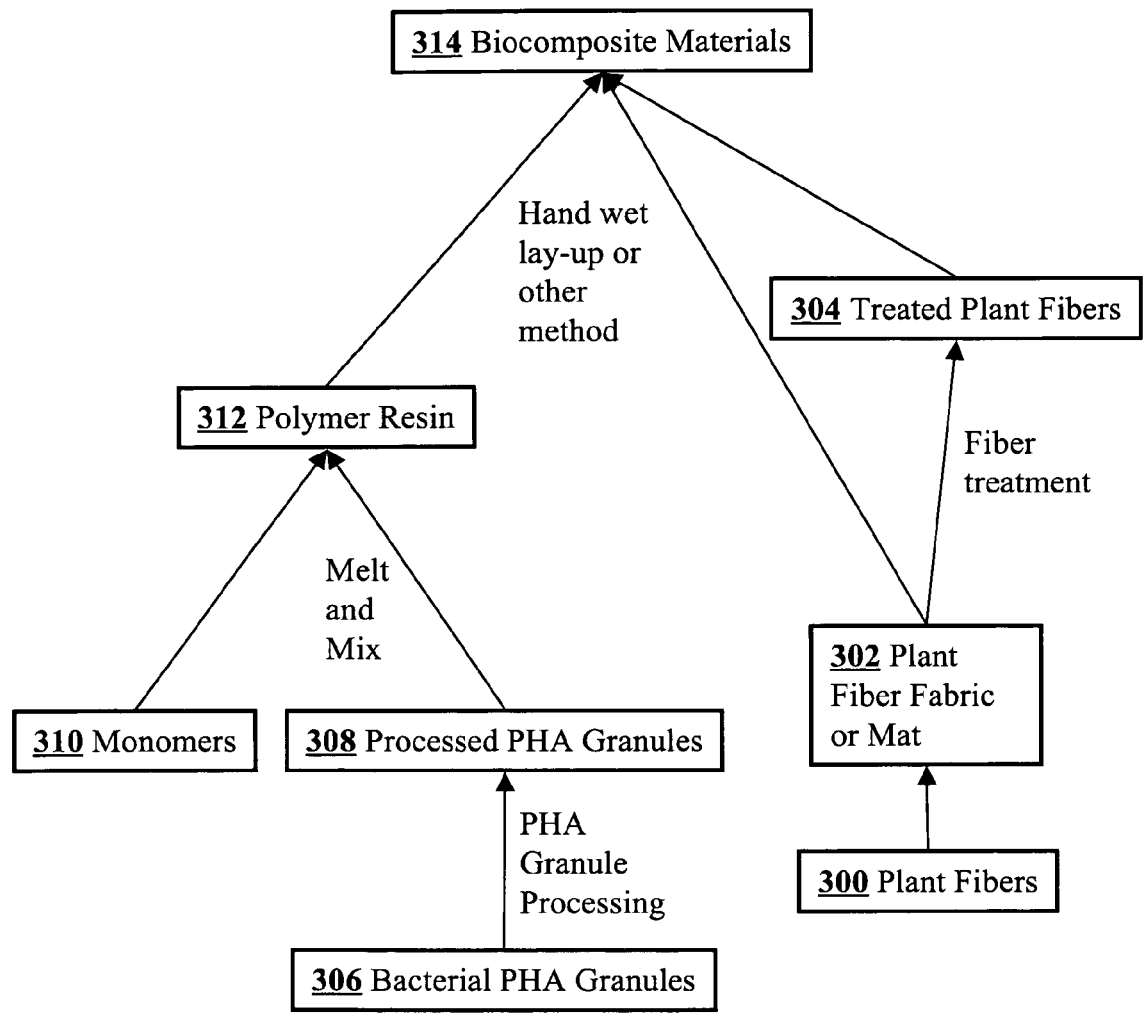
FIG. 3 is a schematic diagram illustrating details of the fabrication of biocomposite materials according to one embodiment of the invention.

FIG. 3 is a schematic diagram illustrating details of the fabrication of biocomposite materials 314 according to one embodiment of the invention. Plant fibers 300 are woven into a fabric or mat 302. To improve various properties of the resulting biocomposite, some of the fibers 302 then may be pretreated to improve subsequent bonding between the fiber and the polymer resin matrix. Treated fibers 304 may then be used, possibly together with untreated fibers 302, to form the resulting biocomposite 314. The bacterial PHA granules 306 may be processed to remove cellular debris, producing processed granules 308, and then melt extruded into thin polymer resin sheets 312, which may be used directly in a hand lay-up with unmodified natural fiber fabric 302 and/or with modified natural fiber fabric 304 to produce biocomposites 314. Alternatively, the extruded PHA sheets can be surface modified to enhance interfacial bonding and then fabricated as a hand lay-up with either modified or unmodified natural fiber fabric. In addition, monomers 310 may be introduced into the PHA to alter its properties, as discussed earlier in relation to FIG. 1.

The pretreating of the natural fibers prior to embedding the fibers in the matrix may involve interfacial property enhancement to improve interfacial bonding. This is typically accomplished by treatment of the fibers with a sizing agent that preferably serves two distinct functions: (1) chemically bind to the fiber surface, and (2) change the chemistry of the fiber surface such that it is thermodynamically compatible with the continuous matrix. This could be accomplished with either low-molecular-weight coupling agents, e.g. trichlorosilanes having alkyl chains of 12 to 18 carbons, or polymeric materials having "sticker" groups distributed along the polymer chain. Treatment with silane coupling agents will enable one to change the surface chemistry of the cellulosic fibers from hydrophilic to hydrophobic, thus improving the compatibility with the resin matrix. An alternative preferred sizing approach is to modify the PHA such that it can chemically bond with the surface of the fibers. This approach has the advantage that the sizing agent is chemically identical to the PHA resin matrix, thus providing more compatible interactions. The processing of the PHA granules may also include modification by treatment with a cyclic anhydride (such as maleic anhydride) and a free radical initiator to form reactive groups capable of covalent bonding to the unmodified textile fiber and producing enhanced mechanical strength.

All natural fibers contain cellulose, which has one primary and two secondary hydroxyl groups per glucose unit, making the fiber surface hydrophilic and making it difficult for hydrophobic materials such as the PHAs to wet the fiber. Since such contact is necessary in order to increase the composite mechanical strength, the preferred practice is to modify the fiber surface with a coupling agent or sizing material. This sizing may be chemically bound to the fiber, with the rest of the sizing molecule composed of units that are compatible with the continuous matrix. For example, cyclic anhydrides will react with the hydroxyl groups at elevated temperature and in the presence of a catalytic amount of strong acid, such as sulfuric or methane sulfonic acid, yielding an ester linkage. One can take advantage of this chemical reaction in two ways. First, reactions of succinic anhydride would occur predominantly with hydroxyl groups on the surface of the same microfibril or fiber, but occasionally this could involve reactions between different fibers. This latter crosslinking reaction should increase the fiber stiffness and tensile strength. Thus, the pretreatment of the fibers may include cross-linking the natural fiber and treatment with a cyclic anhydride (such as succinic anhydride) to improve the bond between the fibers and the PHA. The pretreatment of the natural fiber textile with a cyclic anhydride is preferably performed in the presence of catalytic amounts of acid to promote crosslinking with adjacent textile fibers leading to enhanced textile fiber rigidity. Second, if a small number of anhydride groups were attached at random locations along a polymer chain, their reaction would lead to the polymer chain being attached to the surface of the fibril. If this polymer chain were primarily of the same composition as the surrounding continuous matrix, it would provide an excellent interfacial zone that would enhance the molecular interactions between the fiber and the matrix. Both approaches may be followed.

Although silane coupling agents may be used to modify the fiber surface, preferably modified PHA is used as a sizing. To do so, maleic anhydride may be grafted onto the PHA backbone in the presence of a free-radical initiator and elevated temperature. The grafting occurs through abstraction of a hydrogen atom attached to the PHA backbone. Grafted anhydride groups then can react with pendant hydroxyl groups on the fiber. The advantage of using the modified PHA as a sizing agent is that it matches to the PHA continuous matrix, thus yielding the best wetting. Grafting of maleic anhydride to less than 5% of the PHA's repeating units should be sufficient to significantly increase the hydrophobicity of the fiber after deposition of sizing.

Figure 4:
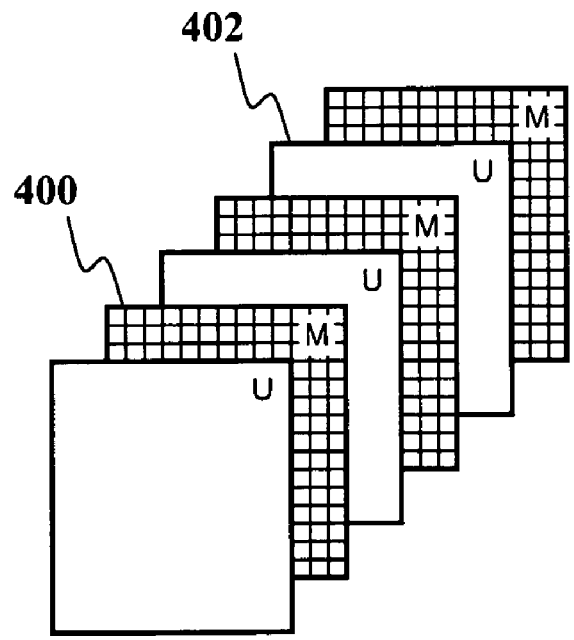
FIG. 4 illustrates a composite layering design combining treated layers and untreated layers according to one embodiment of the invention.

As shown in FIG. 4, the method of producing the biocomposite may also include building up of treated layers and untreated layers. FIG. 4 illustrates a composite layering design combining modified 400 and unmodified 402 fabric layers. The figure shows an example of one pattern [M/U/M/U]. Examples of other potential patterns are [M/M/M/U], [M/M/U/U], [M/U/M/M], [M/U/U/U]. Is also noted that the modified layers may be of different types, e.g., [$M_1$/U/$M_2$/U] or [$M_1$/$M_2$/U/$M_3$]. Preferably, the outer layers of the stratified biocomposite are modified fiber and modified PHA while the inner layers have either unmodified textile or unmodified PHA or both.

The use of differently treated layers helps to achieve good in-service performance as well as rapid and/or optimal degradation and biogas production when taken out of service and put in an anaerobic environment to degrade. Alternation of modified and unmodified fiber reinforcement, for example, permits optimization of the in-service mechanical properties consistent with rapid anaerobic degradation. Through careful selection of fiber types and orientations, along with fiber and PHA modifications, composites may be produced with variable interfacial coupling between matrix and fiber. Strong coupling will lead to higher strength, and weak coupling will provide access for moisture, which is essential to anaerobic degradation.

To balance in-use degradation resistance with rapid anaerobic biodegradation, the composite preferably does not degrade hydrolytically if there is sufficient water, but does degrade enzymatically if water is provided anaerobically. The nature and placement of fiber reinforcement combined with surface modifications may be used to achieve this balance. For example, one class of fibers having strong interfacial interaction with the PHA, thus increasing the strength, may be combined with a second class of weak-bonding fibers to provide regions where the anaerobic degradation could proceed more easily. In the absence of water in well-designed construction, the composite would hold up, but in the presence of water in the landfill, the desired degradation would take place.

A 50% fiber volume fraction, equivalent to 25% unidirectional fibers, produces a composite with high strength and stiffness. To design for a closed loop life-cycle, the optimal fiber volume fraction may change so as to achieve sufficiently good mechanical properties while still allowing the material to degrade rapidly.

In some embodiments, PHA is produced from waste activated sludge amended with volatile fatty acids (VFAs). Aerobic enrichment cultures grown upon the products of anaerobic fermentation—mixtures of VFAs and methane gas—may be used to lower PHA production costs while also conferring significant environmental benefits. These low-cost substrates may be derived from agricultural and industrial fermentations and wastewater treatment. Preferably, fatty acids are produced from biodegradation of agricultural and municipal wastes 108, and production of PHB 112 from the fermented VFAs is produced from biosynthesis using mixed culture enrichments. Large plastic tanks or drums may be used to create sequencing batch reactors at wastewater treatment plants.

Many microorganisms can convert acetate and other VFAs into PHAs, and methanotrophic bacteria can convert methane into PHB. A two-stage production process can be used with: (1) anaerobic fermentation of organic waste to produce VFAs and/or methane, followed by (2) aerobic PHB production using enriched mixed cultures fed fermented supernatant and/or methane. For example, anaerobic thermophilic digestion of activated sludge may produce VFAs followed by aerobic PHB production with *Alcaligenes eutrophus* under nitrogen-limited conditions. PHA production may also be accomplished with nutrient-limited mixed cultures and organic matter derived from domestic wastewater, industrial waste, municipal and food wastes. Reactors for VFA production may be supplemented with intermittent inputs of waste solids. Reactors for PHA production may be aerated and subjected to alternating periods of carbon excess, when VFAs or effluent from the VFA producing batch reactors will be added, and periods of nutrient limitation, when the cells will be starved for key nutrients.

The benefits of PHAs and in particular PHB made using anaerobic fermentation products are that they are: (1) biodegradable, (2) made from a low-cost renewable carbon source, (3) less expensive to produce than PHA materials from sugar or corn starch, (4) produced with lower energy inputs and release lower greenhouse gas emissions over their life-cycle compared to petrochemical plastic materials, and (5) the key to a true cradle-to-cradle carbon cycle. The benefits of natural fibers as a replacement for glass or carbon fibers in biocomposites are that they are (1) annually renewable, (2) have low density, (3) have sufficient mechanical properties for composites useful for the construction industry, (4) are carbon neutral (i.e., carbon absorbed during plant growth equals the carbon released upon degradation after useful service life), and (5) they biodegrade. A biocomposite of PHA and natural fibers produced using the techniques of the present invention enjoys these combined benefits.

The invention claimed is:

1. A method for producing a biocomposite material, the method comprising:
   performing anaerobic microbial biodegradation of waste materials to produce anaerobic degradation products;
   wherein the waste materials comprise waste biocomposite materials;
   wherein the anaerobic degradation products comprise methane and carbon dioxide;
   performing aerobic microbial biosynthesis of PHA polymers from a feedstock using mixed bacterial cultures, wherein the feedstock comprises the methane produced by the anaerobic microbial biodegradation;
   extracting the biosynthesized PHA polymers to obtain PHA granules; and
   fabricating the biocomposite material from the PHA granules and natural fibers;
   wherein fabricating the biocomposite material comprises producing a PHA polymer resin from the PHA granules, and embedding multiple layers of a natural fiber fabric in the PHA polymer resin to form a laminate biocomposite material.

2. The method of claim 1 wherein the anaerobic degradation products comprise volatile fatty acids, and wherein the feedstock comprises the volatile fatty acids.

3. The method of claim 2 wherein the volatile fatty acids comprise acetic and propionic acids.

4. The method of claim 1 wherein the natural fibers are a woven fabric.

5. The method of claim 1 wherein the natural fibers are a mat.

6. The method of claim 1 wherein forming the biocomposite material comprises a hand/wet lay-up process.

7. The method of claim 1 wherein forming the biocomposite material comprises embedding the natural fibers in a matrix produced from the PHA granules.

8. The method of claim 1 wherein fabricating the biocomposite material comprises forming a matrix from monomers and PHA derived from the PHA granules.

9. The method of claim 8 wherein the monomers comprise monomer units selected from the group consisting of hydroxyhexanoate (HH), hydroxybuterate (HB), and hydroxyvalerate (HV).

* * * * *